United States Patent [19]

Garunts et al.

[11] Patent Number: 5,315,834
[45] Date of Patent: May 31, 1994

[54] ROOM AIR ENVIRONMENT CONDITIONER

[76] Inventors: Feliks Garunts, 1422 N. Tamarind Ave., Apt. #8, Los Angeles, Calif. 90028; Robert Darbinyan, D17ur. Sundukyana #87, Yerevan 375012, Armenia, U.S.S.R.

[21] Appl. No.: 930,379

[22] Filed: Aug. 14, 1992

[51] Int. Cl.$^5$ ............................................. F24F 3/16
[52] U.S. Cl. .................................... 62/78; 47/17; 47/60; 62/314
[58] Field of Search ............... 47/17, 60, 65; 62/78, 62/304, 314

[56] References Cited

U.S. PATENT DOCUMENTS

| | | | |
|---|---|---|---|
| 910,400 | 1/1909 | Lischer | 47/17 |
| 3,458,951 | 8/1969 | Martin | 47/17 |
| 3,667,158 | 6/1972 | Privett | 47/17 |
| 3,870,873 | 3/1975 | Mallory | 47/17 |
| 4,144,671 | 3/1979 | Lee | 47/14 |
| 4,400,185 | 8/1983 | Goettl | 55/257 C |
| 4,411,675 | 10/1983 | de Castella | 55/316 |
| 4,440,553 | 4/1984 | Helmus et al. | 55/126 |
| 4,914,858 | 4/1990 | Nijssen et al. | 47/58 |
| 5,136,804 | 8/1992 | Rothem et al. | 47/60 |

FOREIGN PATENT DOCUMENTS

| | | | |
|---|---|---|---|
| 244675 | 5/1965 | Fed. Rep. of Germany | 47/65 |
| 988243 | 1/1983 | U.S.S.R. | 47/60 |
| 1340660 | 9/1987 | U.S.S.R. | 47/60 |

*Primary Examiner*—Ronald C. Capossela
*Attorney, Agent, or Firm*—Felix Garunts

[57] ABSTRACT

A room air environment conditioner for conditioning and improving the air quality in a room. The apparatus includes an enclosed cabinet containing growing plants on trays filled with water to facilitate sprouting and growing of said plants without dirt or sand. The cabinet is separated into light and dark portions to permit regulated growth of said plants. The trays holding the plants have perforated covers upon which are placed a porous material to hold the seeds and the trays are first placed in the dark portion of the cabinet. Once the seeds sprout with roots they are transferred to the lighted portion of the cabinet to grow and generate oxygen. There is an air ionizer located within the cabinet and also a holder containing various chemicals or powders with curative components. A fan blows air through a wetted filter and the cabinet thus changing the oxygen and ionization content of the air in the room, cooling the air and introducing curative powders into the room.

3 Claims, 3 Drawing Sheets

ROOM AIR ENVIRONMENT CONDITIONER

BACKGROUND OF THE INVENTION

This invention relates to an apparatus for treating the environmental air conditions in a room by changing the temperature, humidity, oxygen content, dust content and other elements of the air. This device will provide comfortable and healthy conditions in a home, office and particularly in a hospital room.

Introduction of oxygen into a room from tanks and other oxygen storage devices introduce a controlled amount of oxygen into a living space, but they are very expensive to operate continuously. There is also a known apparatus for growing bean sprouts which contain a housing divided into upper and lower compartments by a horizontally positioned divider plate provided with orifices. An open top sprout container tray is placed within the lower compartment of the housing and the bottom of the sprout containing tray is provided with a drainage opening. (U.S. Pat. No. 4,144,671).

The present invention solves these problems by use of an enclosed air environment conditioner that greatly increases the effectiveness of air treatment and is distinguished by simple construction, low power requirements and safe operation. An embodiment of the invention includes air filters and a negative ion source to clean and ionize the air as it passes through the cabinet.

SUMMARY OF THE INVENTION

The present invention is directed to a room air conditioner which provides a comfortable and healthy climate and air and a device for introducing elements into the air for treatment of asthmatic diseases, general respiratory problems, etc. It is based on a treatment of the air by introduction of oxygen, absorption of carbon dioxide, ionization, dispersion of useful ingredients and smells into the air, and cooling and increasing the humidity of the air. The overall aim is to increase the healthful treatment of the air.

In one form of the invention the air conditioner comprises a cabinet, containing two portions, one dark and one lighted. There are fluorescent lamps for lighting of the upper portion or the cabinet. The lower dark portion is used for germinating seedlings in trays filled with water. Once the seeds have sprouted the tray is moved to the upper lighted portion of the cabinet where the plants grow and produce oxygen. There is also an air ionizer with a cathode network installed within the cabinet. At the entrance of the cabinet is mounted a filter and a fan, which pushes the air through the system. Over the filter is mounted a tank with water which drips into the filter. There is a holder containing various chemicals or ingredients in powdered form at the portion of the cabinet where the air exits from the cabinet.

DESCRIPTION OF THE PREFERRED EMBODIMENT OF THE INVENTION

Figure 1:
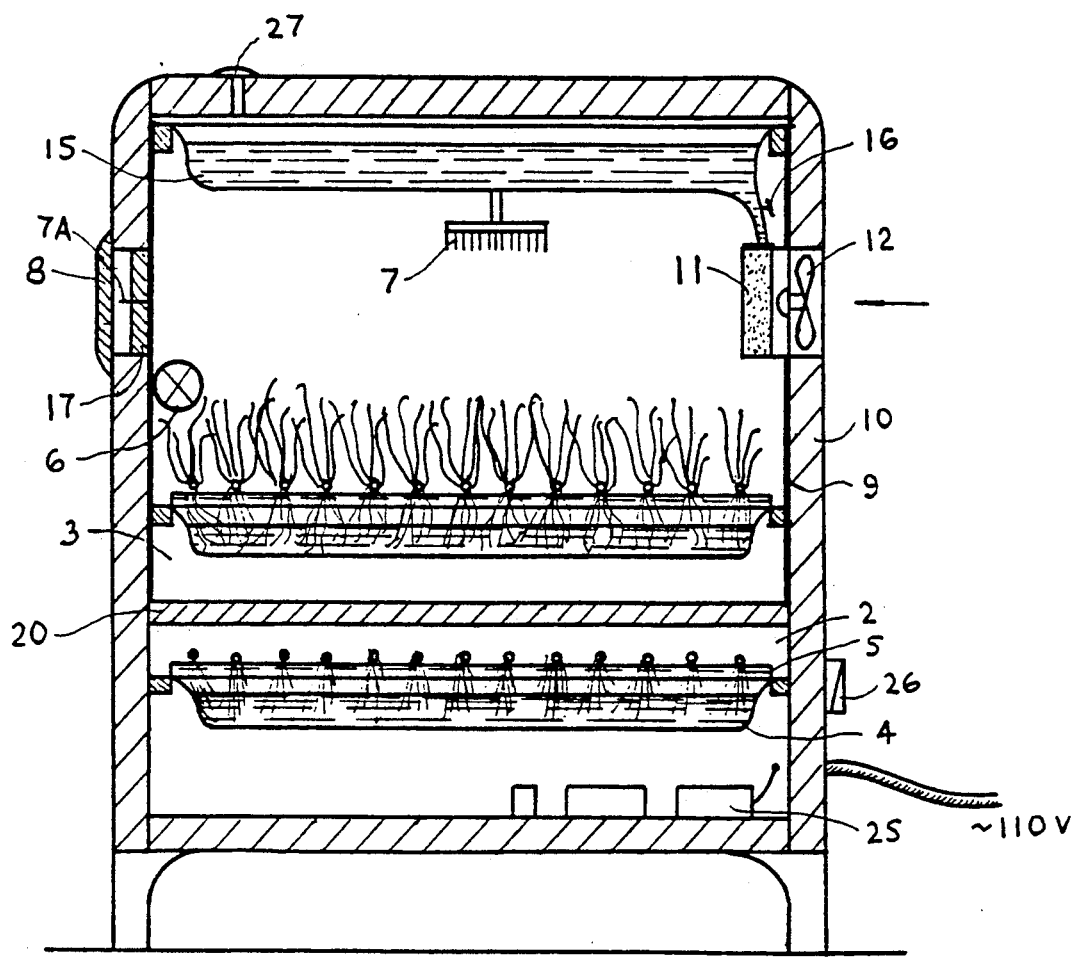
FIG. 1 is an internal schematic type view of the air conditioner embodying the invention for use in a room.

FIG. 1 shows the central air conditioner with a insulated cabinet 1 containing two portions, one dark 2 and one lighted 3. There are rectangular trays 4 containing water and covered by holed plates 5. There are fluorescent lamps 6 for lighting of the upper portion of the cabinet Moreover, there is a negative ion source ionizer with two outlets; one of which is 7 for ionizing air inside the cabinet and the other of which is 7A for ionizing the air as it leaves the cabinet. There is an electrical contact of ionizer with metal sheathing 9 of walls inside the cabinet. Over evaporation filter 11 is mounted a tank 15 filled with water which saturates the filter 11 with water. Hole 27 is used for filling tank 15 with water. The faucet 16 is for regulating the water into the porous element of filter 11. There is a holder 17 in which various chemicals or ingredients in powdered form can be placed at the exit of the cabinet to be introduced into the air.

FIG. 1 also shows an electric power source 25 for the ionizer, fluorescent lamps 6 and the fan controlled by the switches 26.

The invention is operated by setting seeds of barley, oats, clover and other similar seeds on the porous material in the dark lower portion of the air conditioner. They are first wetted and placed on the plates 5 which have holes about $\frac{3}{4}$" in diameter with intervals about $\frac{1}{2}$" covered by hydrophilous materials such as napkins which absorb the water from the tray 4. The optimum quantity of these seeds has been experimentally determined to be one pound for each four square feet. The plates with seeds must be placed on the trays containing water or other feeding solution. The space between plates 5 and the water level can be abut one inch. The door of the air conditioner is then closed for approximately 48-72 hours until sprouting of the roots of the seeds. The trays are then removed from the frame and placed in the upper lighted portion 3. At the same time, new seeds are placed in the dark portion 2 for growing roots of seeds. The door of the air conditioner is then closed and the electricity turned on.

Air from the room passes through the filter 11 and into the cabinet frame where carbon dioxide gas is absorbed by the plants and oxygen is released. The air becomes saturated with oxygen and is ionized as it moves across the ionizer inside the cabinet. Cooling of the air and increasing of its humidity are accomplished by evaporation of the water from tank 15 on the filter 11 when the fan is switched on. Various powdered ingredients such as activized charcoal or sea salt can be inserted into the chamber 17 and dispersed into the room by the moving air.

Figure 2:
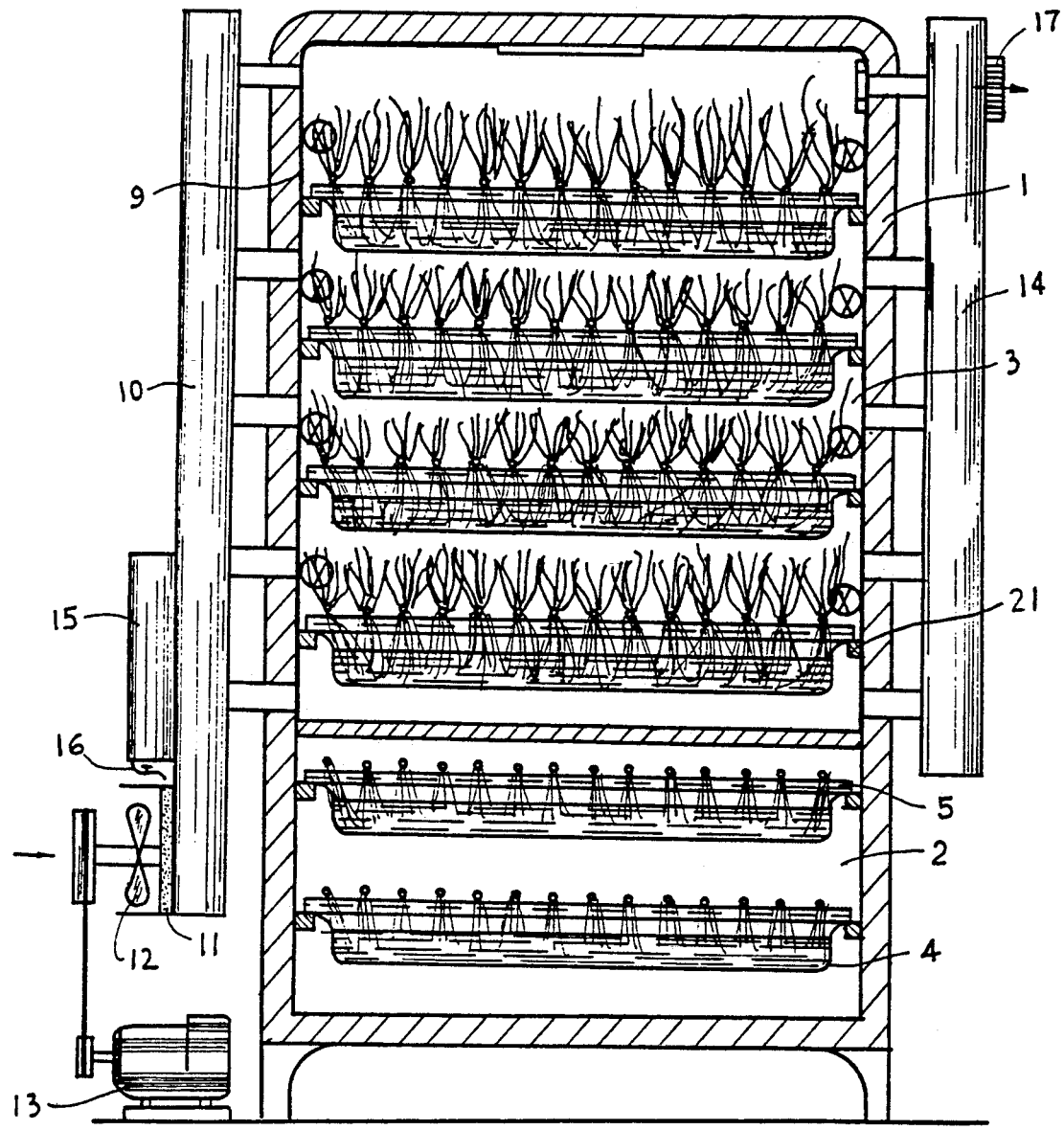
FIG. 2 is an internal schematic type view of the air conditioner embodying the invention which contains multiple trays for use as a central air environment conditioner for large areas.
Figure 3:
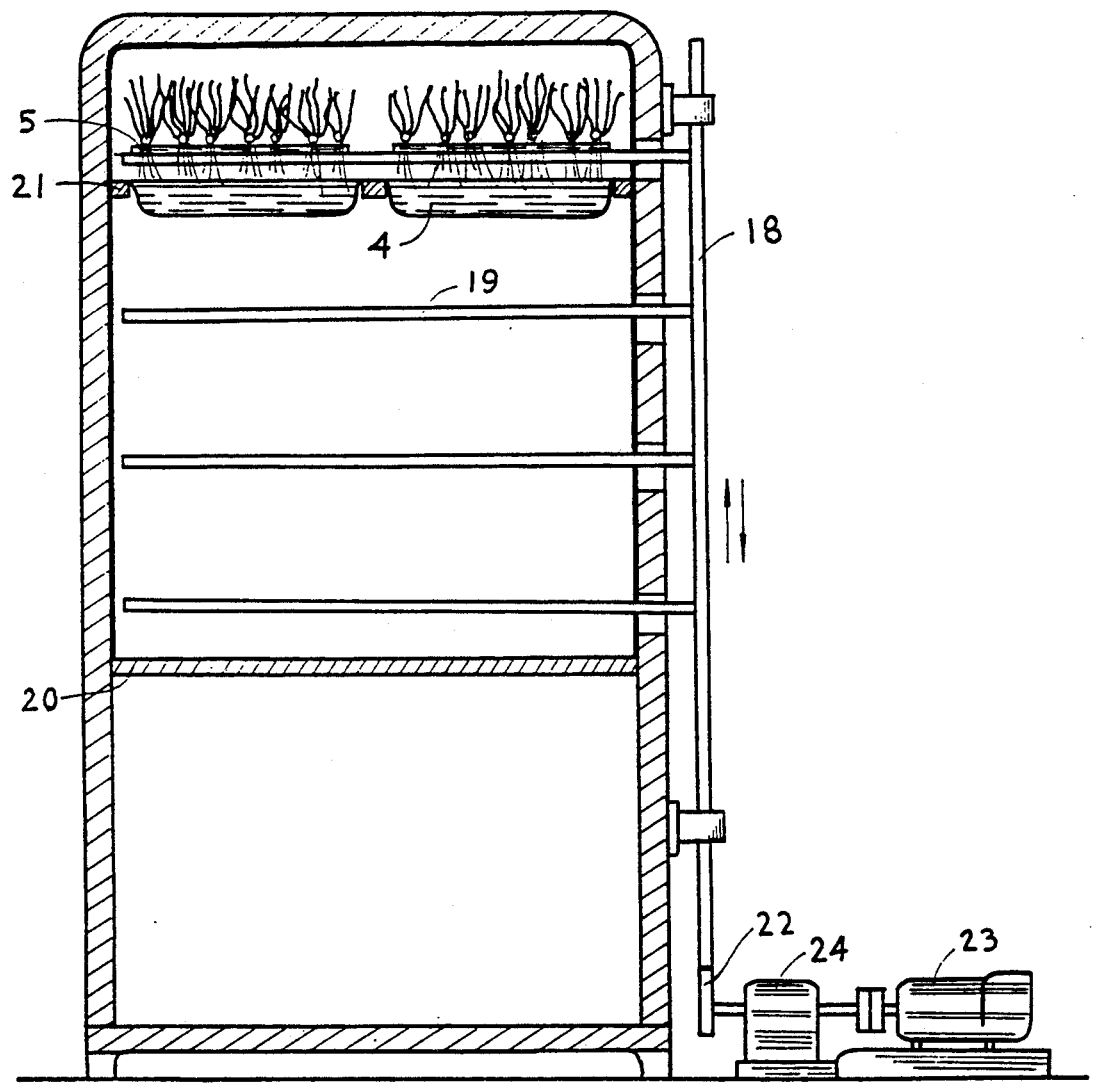
FIG. 3 is an internal schematic type view of the automatic lifting mechanism for lifting plates over the trays within the cabinet.

FIGS. 2 and 3 show further embodiments of the invention for use in a central air environment conditioner in large areas such as a hospital, house or apartment. To intensify the process of photosynthesis by aeration of the roots of the growing plants, there are means of lifting plates 5 in the lighted portion about 2" above the water surface for 20-30 minutes, three to six times periodically during the day while leaving trays 4 in their fixed position on shelves 21. FIG. 3 shows the construction for accomplishing this movement. A carriage 18 with brackets 19 is powdered by an eccentric 22 connected to a motor 23 and gear reducer 24. Plates 5 from FIG. 2 are, periodically lifted above trays 4 only in the lighted portion. As shown in FIG. 3, plates 5 are connected to bars 19 and as bars 19 move up and down, plates 5 also move up and down. This lifting mechanism assists the growth of the seeds by exposing the roots to the air in the cabinet.

The present invention provides for the complex treatment of air. Simultaneous with production of oxygen the conditioner also absorbs unhealthy components of the air such as carbon dioxide, ammonia, sulphureous gas, steams of hard metals and different plastics and organic components.

Besides promoting the photosynteses of the plants, the fluorescent lamps also promote the destruction of bacteria.

When the humidity of the air within the cabinet is high, then the evaporation on the filters is less. In a dry and hot climate the humidity of air in the room is low and evaporation is faster and the cooling of air is also faster. By adding deodorizers to the water of the tank 15 aromatic or curative smells can also be added to the air.

Ionization cleans the air and removes smog. It also charges the air and the curative ingredients from holder 17 with negative polarity which has an effect on biological systems and improves the health of the person breathing it. The charging of dust particles by negative polarity promotes quick precipitation of them on the filter. Moreover the ionization stimulates the growth of plants.

Free air normally contains more than 1000 negative ions per cubic centimeter. In a closed room, ion starvation occurs because the quantity of negative ions is near zero. As external air penetrates the room through the doors and windows, half of these ions are lost and the other half of them stick to walls, furniture etc., being neutralized.

Negative ions which enter the lungs are absorbed into the blood and help treat illness of the lungs, high blood pressure, bronchial asthma and nervousness. Also ionized air is a powerful prophylactic and stimulating factor. Ionization of the air within the cabinet also provides more intensive absorption of carbon dioxide and faster photosynteses of oxygen.

The present invention greatly increases air treatment and is distinguished by simple construction, low power requirements and safe operating conditions. This device will provide comfortable climate and air in the office, home or in a hospital room.

We claim:

1. A room air environment conditioner which comprises:
   a closable container;
   air movement means to move air through said container with an inlet and outlet at opposite sides of said container;
   a tank within said container filled with water;
   a filter wetted from the water in said tank and mounted at the air inlet of the container for cooling said air by evaporation;
   means for growing plants within said container for absorption of carbon dioxide and photosynthesis of oxygen;
   a negative ion source acting within the container when closed being exposed to the air therewithin, thereby causing emission of said ions into the air;
   and a holder containing chemicals in the form of powders selected for their beneficial effects on human health which are placed where the air exits through said container.

2. The room air conditioner of claim 1 wherein, said means for growing plants contain:
   a fluorescent lamp within said container;
   a partition dividing said container to permit a portion only of said container to be lighted by said lamp; and
   trays filled with water and covered by perforated plates with seeds and plants which are placed respectively in the dark and lighted parts of said container.

3. The room air conditioner of claim 1 further comprising an eccentric shaft on a motor which joins and interconnects with the plates of the trays disposed in the lighted part of said container so as to cause lifting of the plant roots from the water.

* * * * *